(12) United States Patent
McMinn et al.

(10) Patent No.: US 7,553,791 B2
(45) Date of Patent: Jun. 30, 2009

(54) HEAVY AROMATICS CONVERSION CATALYST COMPOSITION AND PROCESSES THEREFOR AND THEREWITH

(75) Inventors: Timothy Edward McMinn, Houston, TX (US); David Anthony Stachelczyk, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 253 days.

(21) Appl. No.: 10/982,487

(22) Filed: Nov. 5, 2004

(65) Prior Publication Data

US 2005/0065017 A1 Mar. 24, 2005

Related U.S. Application Data

(63) Continuation-in-part of application No. 10/294,428, filed on Nov. 14, 2002, now Pat. No. 7,148,391.

(51) Int. Cl.
*B01J 29/06* (2006.01)
(52) U.S. Cl. .............. 502/64; 502/60; 502/63; 502/74; 502/66; 502/77; 502/67; 502/69; 502/71
(58) Field of Classification Search .......... 502/60, 502/63, 64, 74, 66, 77, 67, 69, 71
See application file for complete search history.

(56) References Cited

U.S. PATENT DOCUMENTS

| | | | |
|---|---|---|---|
| 3,391,785 A | 7/1968 | Hosokawa et al. | 209/300 |
| 3,832,449 A | 8/1974 | Rosinski et al. | 423/328 |
| 3,914,383 A | 10/1975 | Kirsch et al. | |
| 4,320,242 A | 3/1982 | Onodera et al. | 585/489 |
| 4,341,914 A | 7/1982 | Berger | 585/474 |
| 4,452,769 A | 6/1984 | Chu et al. | 423/329 |
| 4,537,758 A | 8/1985 | Chu et al. | 423/329 |
| 4,539,193 A | 9/1985 | Valyocsik | 423/328 |
| 4,552,738 A | 11/1985 | Rubin | 423/328 |
| 4,552,739 A | 11/1985 | Kühl | 423/328 |
| 4,585,637 A | 4/1986 | Rubin | 423/328 |
| 4,585,746 A | 4/1986 | Valyocsik | 502/62 |
| 4,697,039 A | 9/1987 | Schmidt | 585/477 |
| 4,700,012 A | 10/1987 | Onodera et al. | 585/481 |
| 4,783,568 A | 11/1988 | Schmidt | 585/477 |
| 4,795,550 A | 1/1989 | Sachtler et al. | 208/307 |
| 4,899,011 A | 2/1990 | Chu et al. | |
| 5,021,141 A | 6/1991 | Rubin | 208/46 |
| 5,192,521 A | 3/1993 | Moini et al. | 423/713 |
| 5,726,114 A * | 3/1998 | Chang et al. | 502/64 |
| 5,847,256 A | 12/1998 | Ichioka et al. | 585/470 |
| 5,856,608 A | 1/1999 | Wu et al. | |
| 5,905,051 A | 5/1999 | Wu et al. | 502/60 |
| 5,942,651 A | 8/1999 | Beech, Jr. et al. | 585/475 |
| 6,040,490 A | 3/2000 | Ichioka et al. | 585/475 |
| 6,114,592 A | 9/2000 | Gajda et al. | 585/475 |
| 6,670,517 B1 * | 12/2003 | Abichandani et al. | 585/467 |
| 6,893,624 B2 * | 5/2005 | Lai et al. | 423/705 |
| 7,148,391 B1 * | 12/2006 | Buchanan et al. | 585/475 |
| 2002/0091293 A1 * | 7/2002 | Chang et al. | 585/906 |
| 2002/0198425 A1 | 12/2002 | Mohr | |
| 2004/0097363 A1 * | 5/2004 | Johnson et al. | 502/64 |
| 2005/0020435 A1 * | 1/2005 | Beck et al. | 502/63 |
| 2006/0030478 A1 * | 2/2006 | Raich et al. | 502/66 |

FOREIGN PATENT DOCUMENTS

| | | |
|---|---|---|
| EP | 0 422 727 | 4/1991 |
| EP | 0 677 034 | 10/1995 |
| EP | 0 704 416 | 4/1996 |
| EP | 1 053 987 | 11/2000 |
| EP | 1 061 058 | 12/2000 |
| JP | 9038497 | 2/1997 |
| JP | 9187658 | 7/1997 |
| WO | WO 00/38834 | 7/2000 |
| WO | WO 02/08159 | 1/2002 |
| WO | WO2004/046034 | 6/2004 |
| WO | WO2004/046278 | 6/2004 |
| WO | WO2005/018806 | 3/2005 |

OTHER PUBLICATIONS

Abstract for JP 56045421, published Apr. 25, 1981, entitled "Dealkylation".
Abstract for JP 61176539, published Aug. 8, 1986, entitled "Dealkylation".

* cited by examiner

*Primary Examiner*—Elizabeth D Wood
(74) *Attorney, Agent, or Firm*—Andrew B. Griffis

(57) ABSTRACT

A catalyst composition, a process for producing the composition and a process for the conversion of a feedstock containing $C_9+$ aromatic hydrocarbons to produce a resulting product containing lighter aromatic products and less than about 0.5 wt % of ethylbenzene based on the weight of $C_8$ aromatics fraction of the resulting product. The $C_9+$ aromatic hydrocarbons are converted under the transalkylation reaction conditions to a reaction product containing xylene. The catalyst composition comprises (i) an acidity component having an alpha value of at least 300; and (ii) a hydrogenation component having hydrogenation activity of at least 300. The composition can be produced by to incorporating at least one hydrogenation component into an acidity component having an alpha value of at least 300.

2 Claims, No Drawings

HEAVY AROMATICS CONVERSION CATALYST COMPOSITION AND PROCESSES THEREFOR AND THEREWITH

CROSS REFERENCE TO RELATED APPLICATIONS

This application is a continuation-in-part of application Ser. No. 10/294,428, filed Nov. 14, 2002 now U.S. Pat. No. 7,148,391, the disclosure which is incorporated by reference in its entirety.

FIELD

The invention relates to a catalyst composition useful for converting heavy aromatics, specifically $C_9+$ aromatics, to lighter aromatic products, particularly benzene, toluene and xylenes (hereinafter collectively referred to as BTX), to a process for producing the composition and to a process for using the composition in a heavy aromatics conversion process.

BACKGROUND

A source of benzene and xylenes is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains BTX, along with ethylbenzene.

Refineries have also focused on the production of benzene and xylenes by transalkylation of $C_9+$ aromatics and toluene over noble metal-containing zeolite catalysts. High value petrochemical products, such as benzene and xylenes, together with ethylbenzene are formed during the transalkylation of $C_9+$ aromatics and toluene over catalysts containing noble metals. The resulting translation product is subjected to further separation of non-aromatics, benzene, $C_8$ aromatics (i.e., ethylbenzene, para-xylene, meta-xylene, and ortho-xylene), unreacted toluene, and unreacted $C_9+$ aromatics. Usually, the $C_8$ aromatics product is subjected to further separation to produce xylenes, particularly, para-xylene. Lowering the amount of ethylbenzene in the $C_8$ aromatics improves efficiency of xylene recovery. Therefore, there are strong economic and technical incentives to decrease the ethylbenzene concentration in the transalkylation product. The amount of ethylbenzene in the transalkylation product depends primarily on (a) the feedstock composition and (b) the transalkylation catalyst and the transalkylation conditions. Typically, the $C_9+$ aromatics feedstock and/or the toluene feed contains ethylbenzene as an impurity ranging from 0.001 to 4 wt % based on total weight of the feed. Other than the ethylbenzene in the feedstock, ethylbenzene can be formed during transalkylation process from a feed comprising ethyl-containing $C_9+$ aromatics and from various side-reactions.

One solution to the problem of the ethylbenzene in the transalkylation product during the transalkylation of heavy aromatics is disclosed in U.S. Pat. No. 5,942,651 and involves the steps of contacting a feed comprising $C_9+$ aromatic hydrocarbons and toluene under transalkylation reaction conditions with a first catalyst composition comprising a zeolite having a constraint index ranging from 0.5 to 3, such as ZSM-12, and a hydrogenation component. The effluent resulting from the first contacting step is then contacted with a second catalyst composition which comprises a zeolite having a constraint index ranging from 3 to 12, such as ZSM-5, and which may be in a separate bed or a separate reactor from the first catalyst composition to produce a transalkylation reaction product comprising benzene and xylene. The ethylbenzene in the feed and/or the ethylbenzene formed during transalkylation process is partially destroyed by dealkylation of ethylbenzene to benzene and ethylene.

U.S. Pat. No. 5,905,051 discloses a process for converting a hydrocarbon stream such as, for example, a $C_9+$ aromatic compound to $C_6$ to $C_8$ aromatic hydrocarbons, such as xylenes, by contacting the stream with a catalyst system comprising a first catalyst composition and a second catalyst composition, wherein said catalyst compositions are present in separate stages and are not physically mixed or blended and wherein said first catalyst composition is a metal-promoted, alumina- or silica-bound zeolite beta, and said second catalyst composition is ZSM-5 having incorporated therein an activity promoter selected from the group consisting of silicon, phosphorus, sulfur, and combinations thereof. According to the '051 patent, the use of the separate catalytic stages improves the conversion of $C_9+$ aromatic compounds and naphthalenes to xylenes and decreases the amount of undesirable ethylbenzene in the product. The ethylbenzene in the '051 product is about 3-7 wt % of ethylbenzene based on the weight of $C_8$ aromatics fraction of the resulting product.

It has now been found that a catalyst system comprising a molecular sieve exhibits enhanced acidity and hydrogenation activity for substantial removal of ethyl-group containing aromatic compounds in $C_9+$ aromatic feeds without overall reduction in the conversion of the $C_9+$ feed to useful compounds, such as xylenes.

SUMMARY

In one embodiment, the invention relates to a catalyst composition comprising:
i) an acidity component having an alpha value of at least 300; and
ii) a hydrogenation component having hydrogenation activity of at least 300.

In another embodiment, the invention relates to a process for producing a catalyst composition comprising:
i) contacting an acidity component having an alpha value of at least 300 with at least one hydrogenation component under a condition sufficient to incorporate said hydrogenation component into said acidity component to form a modified acidity component; and
ii) calcining said modified acidity component to produce said catalyst having hydrogenation activity of at least 300.

In another embodiment, the invention relates to a process for the conversion of a feedstock containing $C_9+$ aromatic hydrocarbons to produce a resulting product containing lighter aromatic products and less than about 0.5 wt % of ethylbenzene based on the weight of $C_8$ aromatics fraction of said resulting product, said process comprising contacting said feedstock under transalkylation reaction conditions with a catalyst composition comprising: (i) an acidity component having an alpha value of at least 300; and (ii) a hydrogenation component having hydrogenation activity of at least 300, the $C_9+$ aromatic hydrocarbons being converted under said transalkylation reaction conditions to a reaction product containing xylenes. Preferably, the aromatic product contains less than about 0.3 wt % of ethylbenzene based on the weight of $C_8$ aromatics fraction of said resulting product. More preferable, the aromatic product contains less than about 0.2 wt % of ethylbenzene based on the weight of $C_8$ aromatics fraction of said resulting product.

Preferably, the acidity component comprises a molecular sieve selected from the group consisting of one or more of a first molecular sieve having a MTW structure, a molecular sieve having a MOR structure, and a porous crystalline inorganic oxide material having an X-ray diffraction pattern including d-spacing maxima (Å) at 12.4±0.25, 6.9±0.15, 3.57±0.07 and 3.42±0.07. More preferably, the catalyst comprises a molecular sieve ZSM-12. Alternatively, the porous crystalline inorganic oxide material is selected from the group consisting of one or more of MCM-22, PSH-3, SSZ-25, MCM-36, MCM-49 and MCM-56.

In another embodiment, the catalyst comprises second molecular sieve having a constraint index ranging from 3 to 12. Preferably, the second molecular sieve is ZSM-5. Preferably, the catalyst comprises two molecular sieves, the first molecular sieve is ZSM-12, and the second molecular sieve is ZSM-5. Conveniently, the catalyst composition is particulate and the first and second molecular sieves are each contained in the same catalyst particles.

Preferably, the hydrogenation component is selected from the group consisting of one or more of a Group VIIIB and Group VIIB metal. More preferably, the hydrogenation component is selected from the group consisting of one or more of rhenium, platinum, and palladium.

Typically, the feed contains benzene or toluene. In a further aspect, the invention resides in a process for producing benzene comprising the steps of: (a) reacting $C_9$+ aromatic hydrocarbons and toluene under transalkylation reaction conditions over a catalyst composition comprising (i) an acidity component having an alpha value of at least 300; and (ii) a hydrogenation component having hydrogenation activity of at least 300, to produce a resulting product stream comprising benzene and xylenes; and (b) distilling the benzene from said product stream to obtain a benzene product. Preferably, the aromatic product contains less than about 0.5 wt % of ethylbenzene based on the weight of $C_8$ aromatics fraction of said resulting product. More preferable, the aromatic product contains less than about 0.3 wt % of ethylbenzene based on the weight of $C_8$ aromatics fraction of said resulting product. More preferable, the aromatic product contains less than about 0.2 wt % of ethylbenzene based on the weight of $C_8$ aromatics fraction of said resulting product.

In a further aspect, the invention resides in a process for processing $C_9$+ aromatic hydrocarbons at least at a rate of ten kilograms per hour.

DETAILED DESCRIPTION OF THE EMBODIMENTS

In a preferred embodiment, this invention provides a catalyst composition comprises (i) an acidity component having an alpha value of at least 300, perferably the alpha value of at least 400, more preferably the alpha value of at least 500; and (ii) a hydrogenation component having hydrogenation activity of at least 300, perferably the hydrogenation activity of at least 500, more preferably the hydrogenation activity of at least 1000.

Preferably, the acidity component comprises a first molecular sieve selected from the group consisting of one or more of a molecular sieve having a MTW structure, a molecular sieve having a MOR structure, and a porous crystalline inorganic oxide material having an X-ray diffraction pattern including d-spacing maxima (Å) at 12.4±0.25, 6.9±0.15, 3.57±0.07 and 3.42±0.07. More preferably, the catalyst comprises a molecular sieve ZSM-12. Alternatively, the porous crystalline inorganic oxide material is selected from the group consisting of MCM-22, PSH-3, SSZ-25, MCM-36, MCM-49 and MCM-56.

In another embodiment, the catalyst comprises second molecular sieve having a constraint index ranging from 3 to 12. Preferably, the second molecular sieve is ZSM-5. Preferably, the catalyst comprises two molecular sieves, the first molecular sieve is ZSM-12, and the second molecular sieve is ZSM-5. Conveniently, the catalyst composition is particulate and the first and second molecular sieves are each contained in the same catalyst particles.

Preferably, the hydrogenation component is selected from the group consisting of one or more of a Group VIIIB and Group VIIB metal. More preferably, the hydrogenation component is selected from the group consisting of one or more of rhenium, platinum, and palladium.

In another embodiment, the invention relates to a process for producing a catalyst composition comprising:

i) contacting an acidity component having an alpha value of at least 300 with at least one hydrogenation component under a condition sufficient to incorporate said hydrogenation component into said acidity component to form a modified acidity component; and ii) calcining said modified acidity component to produce said catalyst having hydrogenation activity of at least 300.

Preferably, said hydrogenation component is incorporated into said acidity component by ion-exchange, incipient wetness impregnation, solid-state reaction, or combinations of two or more thereof. More preferably, said hydrogenation component is incorporated into said acidity component by ion exchange, and/or incipient wetness impregnation.

In another embodiment, the invention relates to a process for the conversion of a feedstock containing $C_9$+ aromatic hydrocarbons to produce a resulting product containing lighter aromatic products and less than about 0.5 wt % of ethylbenzene based on the weight of $C_8$ aromatics fraction of said resulting product, said process comprising contacting said feedstock under transalkylation reaction conditions with a catalyst composition comprising: (i) an acidity component having an alpha value of at least 300; and (ii) a hydrogenation component having hydrogenation activity of at least 300, the $C_9$+ aromatic hydrocarbons being converted under said transalkylation reaction conditions to a reaction product containing xylenes. Preferably, the aromatic product contains less than about 0.3 wt % of ethylbenzene based on the weight of $C_8$ aromatics fraction of said resulting product. More preferable, the aromatic product contains less than about 0.2 wt % of ethylbenzene based on the weight of $C_8$ aromatics fraction of said resulting product.

As used herein, the term "lighter aromatic products" is defined to mean aromatic molecules in products having fewer carbon atoms than the carbon atoms of aromatic molecules in the feedstock. For example, para-xylene, one of the resulting products of $C_9$+ transalkylation with toluene and/or benzene, has 8 carbon atoms which is less than 9 or more carbon atoms in $C_9$+ aromatic molecules.

Catalyst Composition

The catalyst composition used in the process of the invention comprises:

(i) an acidity component having an alpha value of at least 300; and (ii) a hydrogenation component having hydrogenation activity of at least 300, The acidity component is a material of having an alpha value of at least 300, such as, silica-alumina, acidic zicoria, a molecular sieve selected from the group consisting of a molecular sieve having a MTW structure, a molecular sieve having a MOR structure, and a porous crystalline inorganic oxide material having an X-ray diffraction pattern including d-spacing maxima (Å) at 12.4±0.25, 6.9±0.15, 3.57±0.07 and 3.42±0.07.

With regard to the molecular sieve, ZSM-12 is more particularly described in U.S. Pat. No. 3,832,449. Mordenite occurs naturally but may also be used in one of its synthetic forms, such as TEA-mordenite (i.e., synthetic mordenite prepared from a reaction mixture comprising a tetraethylammonium directing agent), which is disclosed in U.S. Pat. Nos. 3,766,093 and 3,894,104. Examples of suitable porous crystalline inorganic oxide materials having the defined X-ray diffraction pattern include MCM-22, PSH-3, SSZ-25, MCM-36, MCM-49 or MCM-56. MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575 and MCM-56 is described in U.S. Pat. No. 5,362,697. The entire contents of each of the aforementioned patents are incorporated herein by reference.

With regard to the molecular sieve, suitable materials having a constraint index of 3 to 12 include ZSM-5, ZSM-11, ZSM-22, ZSM-23, ZSM-35, ZSM-48, ZSM-57 and ZSM-58. ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573. ZSM-57 is described in U.S. Pat. No. 4,873,067. ZSM-58 is described in U.S. Pat. No. 4,698,217. Constraint index and a method for its determination are described in U.S. Pat. No. 4,016,218. The entire contents of each of the aforementioned patents are incorporated herein by reference.

Typically, the second molecular sieve constitutes from 0 to 95 wt %, such as from in excess of 20 to 80 wt % based on the total weight of the first and second molecular sieves in the catalyst composition.

Where the first molecular sieve is ZSM-12, the ZSM-12 can have a composition involving the molar relationship:

$$X_2O_3:(n)YO_2$$

wherein X is a trivalent element, such as aluminum, boron, iron, indium and/or gallium, preferably aluminum; Y is a tetravalent element, such as silicon, tin and/or germanium, preferably silicon; and n is less than 75, such as from 20 to less than 60. The ZSM-12 may further be selected so as to have an average crystal size of less than 0.1 micron, such as about 0.05 micron, and a Diffusion Parameter, $D/r^2$, for mesitylene of at least $1000\times10^{-6}\,sec^{-1}$, such as at least $2000\times10^{-6}\,sec^{-1}$, when measured at a temperature of 100° C. and a mesitylene pressure of 2 torr.

As used herein, the Diffusion Parameter of a particular porous crystalline material is defined as $D/r^2\times10^6$, wherein D is the diffusion coefficient ($cm^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt^2/r)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The ZSM-12 used as the first molecular sieve may also be arranged to have an Alpha value of at least 150, such as at least 300. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

ZSM-12 having the composition, crystal size, Diffusion Parameter and alpha value described in the preceding paragraphs can be produced by crystallization of a synthesis mixture containing sources of alkali or alkaline earth metal (M) cations, normally sodium, an oxide of a trivalent element (X), normally alumina, an oxide of a tetravalent element (Y), normally silica, methyltriethylammonium ions (R), normally present as the iodide salt, hydroxyl ions and water. The synthesis mixture may have a composition, expressed in terms of mole ratios of oxides, as follows:

| Component | Useful | Preferred |
| --- | --- | --- |
| $YO_2/X_2O_3$ | 20-100 | 40-80 |
| $H_2O/YO_2$ | 10-100 | 15-40 |
| $OH^-/YO_2$ | 0.1-0.6 | 0.15-0.4 |
| $R/YO_2$ | 0.1-0.6 | 0.15-0.4 |
| $M/YO_2$ | 0.1-0.6 | 0.15-0.4 |

The synthesis mixture may also contain nucleating seeds of ZSM-12 and, where such seeds are present, they typically constitute 0.05-5 wt % of the mixture. Crystallization of the synthesis mixture may be carried out under either stirred or static conditions, preferably stirred conditions, at a temperature of 160° C. or less, such as 140 to 160° C. for 48 to 500 hours, whereafter the resultant ZSM-12 crystals are separated from the mother liquor and recovered It may be desirable to incorporate each molecular sieve in the catalyst composition with another material that is resistant to the temperatures and other conditions employed in the transalkylation process of the invention. Such materials include active and inactive materials and synthetic or naturally occurring zeolites, as well as inorganic materials such as clays, silica and/or metal oxides such as alumina. The inorganic material may be either naturally occurring, or in the form of gelatinous precipitates or gels including mixtures of silica and metal oxides.

Use of a material in conjunction with each molecular sieve, i.e. combined therewith or present during its synthesis, which itself is catalytically active, may change the conversion and/or selectivity of the catalyst composition. Inactive materials suitably serve as diluents to control the amount of conversion so that transalkylated products can be obtained in an economical and orderly manner without employing other means for controlling the rate of reaction. These catalytically active or inactive materials may be incorporated into, for example, naturally occurring clays, e.g. bentonite and kaolin, to improve the crush strength of the catalyst composition under commercial operating conditions. It is desirable to provide a catalyst composition having good crush strength because in commercial use, it is desirable to prevent the catalyst composition from breaking down into powder-like materials.

Naturally occurring clays that can be composited with the molecular sieve's as a binder for the catalyst composition include the montmorillonite and kaolin family, which families include the subbentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieve's can be composited with a porous matrix binder material, such as an inorganic oxide selected from the group consisting of silica, alumina, zirconia, titania, thoria, beryllia, magnesia, and combinations thereof, such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. It may also be advantageous to provide at least a part of the foregoing porous matrix binder material in colloidal form to facilitate extrusion of the catalyst composition.

Each molecular sieve is usually admixed with the binder or matrix material so that the final catalyst composition contains the binder or matrix material in an amount ranging from 5 to 90 wt %, and typically from 10 to 60 wt %.

In the process of the invention, the first and second molecular sieves are contained in the same catalyst bed. Normally this is achieved either by physically mixing separate particles of the individual molecular sieves, preferably in bound form, or by co-extruding a mixture of the molecular sieves, typically with a binder, such that each particle of the final catalyst composition contains both the first and second molecular sieves. Alternatively, the particles of one of the first and second molecular sieves can be formed as a binder for the other of said first and second molecular sieves, such as is described in International Patent Publication No. WO 97/45198, the entire contents of which are incorporated herein by reference.

At least the first molecular sieve, and preferably each molecular sieve, in the catalyst composition has associated therewith at least one hydrogenation component, such as tungsten, vanadium, molybdenum, rhenium, chromium, manganese, a metal selected from Group IB, IIB, IIIB, IVB, VB, VIB, VII B, and VIIIB of the Periodic Table of the Elements (CAS version, 1979), or mixtures thereof. Useful Group VIIIB metals include iron, ruthenium, osmium, nickel, cobalt, rhodium, iridium, and noble metals such as platinum, rhenium, or palladium. Preferably, the hydrogenation component is palladium, platinum or rhenium.

The amount of the hydrogenation component is selected according to a balance between hydrogenation activity and catalytic functionality. Less of the hydrogenation component is required when the most active metals such as platinum are used as compared to palladium, which does not possess such strong hydrogenation activity. Generally, the catalyst composition contains less than 10 wt % of the hydrogenation component and typically from 0.01 wt % to 2 wt % of said component.

The hydrogenation component can be incorporated into the catalyst composition by co-crystallization, exchanged into the composition to the extent a Group IIIA element, e.g., aluminum, is in the molecular sieve structure, impregnated therein, or mixed with the molecular sieve and binder. Such component can be impregnated in or on the molecular sieve, for example in the case of platinum, by treating the molecular sieve with a solution containing a platinum metal-containing ion. Suitable platinum compounds for impregnating the catalyst with platinum include chloroplatinic acid, platinous chloride and various compounds containing the platinum ammine complex, such as $Pt(NH_3)_4Cl_2 \cdot H_2O$.

Alternatively, a compound of the hydrogenation component may be added to the molecular sieve when it is being composited with a binder, or after the molecular sieve and binder have been formed into particles by extrusion or palletizing.

The hydrogenation component may also be arranged to have a hydrogenation activity of hydrogenation value of at least 300, such as at least 500, preferably at least 1000. The hydrogenation function is measured by comparing the amount of ethylene to the amount of ethane in the transalkylation product. Ethylene is formed in the transalkylation process by the dealkylation of ethyl-substituted aromatic molecules and by the cracking of aliphatic and naphthenic hydrocarbons. The hydrogenation component is designed to saturate these ethylene molecules to ethane before they can engage in side reactions. The better the hydrogenation component the less ethylene will be present relative to ethane in the transalkylation product. The hydrogenation value is defined as the ratio of ethane over ethylene. The experimental conditions of the test used herein include a constant temperature of 412° C., a pressure of 2170 kPAa, a hydrogen to hydrocarbon molar ratio of 2, a toluene/1,4-methylethylbenzene ratio of 2, and a WHSV of 2.7 $h^{-1}$. The hydrogenation value, measured by ethane/ethylene ratio, is calculated by the molar percentage of ethane in the product divided by the molar percentage of ethylene in the product.

After treatment with the hydrogenation component, the molecular sieve is usually dried by heating at a temperature of 65° C. to 160°, typically 110 to 143° C., for at least 1 minute and generally not longer than 24 hours, at pressures ranging from 100 to 200 kPAa. Thereafter, the molecular sieve may be calcined in a stream of dry gas, such as air or nitrogen, at temperatures of from 260° to 650° C. for 1 to 20 hours. Calcination is typically conducted at pressures ranging from 100 to 300 kPAa and a WHSV of about 0.002 to about 20 $h^{-1}$.

Prior to use, steam treatment of the catalyst composition may be employed to minimize the aromatic hydrogenation activity of the catalyst composition. In the steaming process, the catalyst composition is usually contacted with from 5 to 100% steam, at a temperature of at least 260° to 650° C. for at least one hour, specifically 1 to 20 hours, at a pressure of 100 to 2590 KPAa and a WHSV of about 0.002 to about 20 $h^{-1}$.

In addition, prior to contacting the catalyst composition with the hydrocarbon feed, the hydrogenation component can be sulfided. This is conveniently accomplished by contacting the catalyst with a source of sulfur, such as hydrogen sulfide, at a temperature ranging from about 320 to 480° C. The source of sulfur can be contacted with the catalyst via a carrier gas, such as hydrogen or nitrogen.

After contacting the catalyst composition with the hydrocarbon feed, the catalyst may be deactivated due to coking or metal agglomerization. The deactivated catalyst can be regenerated conveniently by coke burning with a stream comprising oxygen or oxygen containing compounds, such as, ozone, oxochlorine, carbon disxide or the like, metal re-dispersing using oxdization-reduction cycle, oxochloride treatment or the like, washing with liquid hydrocarbons or aqueous solution of inorganic and/or organic chemical compounds, such as, water, ethanol, acetone, or the like, or rejuventaion with a stream comprising hydrogen. Regeneration or rejuvention can be performed at a temperature range from ambience to about 600° C., a pressure range of about 100 to about 5000 KPAa, and WHSV of about 0.2 to about 100 $h^{-1}$.

The Feed

The aromatic feed used in the process of the invention comprises ethylbenzene and one or more aromatic compounds containing at least 9 carbon atoms. Specific $C_9+$ aromatic compounds found in a typical feed include mesitylene (1,3,5-trimethylbenzene), durene (1,2,4,5-tetramethylbenzene), hemimellitene (1,2,4-trimethylbenzene), pseudocumene (1,2,4-trimethylbenzene), 1,2-methylethylbenzene, 1,3-methylethylbenzene, 1,4-methylethylbenzene, propyl-substituted benzenes, butyl-substituted benzenes, and dimethylethylbenzenes. Suitable sources of the $C_9+$ aromatics are any $C_9+$ fraction from any refinery process that is rich in aromatics. This aromatics fraction contains a substantial proportion of $C_9+$ aromatics, e.g., at least 80 wt % $C_9+$ aromatics, wherein preferably at least 80 wt %, and more preferably more than 90 wt %, of the hydrocarbons will range from $C_9$ to $C_{12}$. Typical refinery fractions which may be useful include catalytic reformate, FCC naphtha or TCC naphtha.

The feed may also comprise benzene or toluene. Thus, in one practical embodiment, the feed to the transalkylation reactor comprises ethylbenzene, $C_9+$ aromatics hydrocarbons and toluene. The feed may also include recycled/unreacted/produced benzene, toluene, ethylbenzene, and $C_9+$ aromatics that is obtained by distillation of the effluent product of the transalkylation reaction itself. Typically, toluene constitutes from about 5 to about 90 wt % and $C_9+$ constitutes from about 10 to about 95 wt %. In a typical light feed, toluene constitutes from about 40 to about 90 wt %, such as from 50 to 70 wt % of the entire feed, wheras the $C_9+$ aromatics component constitutes from 10 to 60 wt %, such as from 30 to 50 wt %, of the entire feed to the transalkylation reaction zone. In a typical heavy feed, toluene constitutes from about 15 to about 50 wt %, such as from 25 to 40 wt % of the entire feed, wheras the $C_9+$ aromatics component constitutes from 50 to 85 wt %, such as from 60 to 75 wt %, of the entire feed to the transalkylation reaction zone.

Hydrocarbon Conversion Process

The process can be conducted in any appropriate reactor including a radial flow, fixed bed, continuous flow or fluid bed reactor. The transalkylation reaction conditions typically include a temperature ranging from about 343° to about 510° C., such as from about 400° to about 454° C.; a pressure from about 380 to about 4240 kPAa, such as from about 1480 to about 3550 kPAa; a hydrogen to hydrocarbon molar ratio from about 1 to about 5, such as from about 1 to about 3 and a WHSV of about 0.2 to about 20 $h^{-1}$, such as from 1 to about 5 $h^{-1}$. The transalkylation reaction conditions are sufficient to convert the heavy aromatic feed to a product containing substantial quantities of $C_6$-$C_8$ aromatic compounds, such as benzene, toluene and xylenes, especially benzene and xylene. The transalkylation reaction conditions also are sufficient to convert the ethylbenzene in the feed to benzene and ethane.

The invention will now be more particularly described with reference to the following Examples.

EXAMPLE 1

Catalyst Preparation

A small crystal, high activity ZSM-12 was synthesized from a mixture comprising 11280 g of water, 1210 g of methyltriethylammonium chloride (MTEACl), 1950 g of Ultrasil PM available from Degussa, 229 g of sodium aluminate solution (45%), and 364 g of 50% sodium hydroxide solution. The mixture had the following molar composition:

$SiO_2/Al_2O_3=50$
$H_2O/SiO_2=22$
$OH^-/SiO_2=0.2$
$Na^+/SiO_2=0.2$
$MTEACl/SiO_2=0.26$

The mixture was reacted at 160° C. in a 5-gal autoclave with stirring at 150 RPM for 144 hours. The product was filtered, washed with deionized (DI) water and dried at 120° C. The XRD pattern of the as-synthesized material showed the typical pure phase of ZSM-12 topology. The SEM of the as-synthesized material showed that the material was composed of agglomerates of small crystals (with an average crystal size of about 0.05 microns).

The as-synthesized crystals were converted into the hydrogen form by two ion exchanges with ammonium nitrate solution at room temperature, followed by drying at 120° C. and calcination at 540° C. for 6 hours. The resulting ZSM-12 crystals had a $SiO_2/Al_2O_3$ molar ratio of 44.98, an Alpha value of 500 and a $D/r^2$ for mesitylene of greater than 5000× $10^{-6}$ $sec^{-1}$ at a temperature of 100° C. and a mesitylene pressure of 2 torr.

A mixture containing 65 wt % of the ZSM-12 produced as above, 15 wt % ZSM-5, and 20 wt % alumina was extruded into pellets 1.3 mm in length and having a quadrulobe cross-section. The pellets were dried at 120° C. then calcined in nitrogen for 3 hours at 480° C. This material was then exchanged with ammonium nitrate, dried at 120° C. and then calcined in air for 6 hours at 540° C. 0.5 wt % Re was then added to the catalyst by incipient wetness impregnation from an aqueous solution of tetraammine rhenium nitrate. The impregnated material was dried at 120° C. then calcined in air for 6 hours at 350° C. to produce a final catalyst.

EXAMPLE 2

Three grams of the resultant catalyst composition from example 1 was used to effect transalkylation of a mixture of toluene/$C_9+$ aromatic hydrocarbon mixture having the composition given in Table 1 at a temperature of about 412° C., a pressure of 2170 kPAa, a hydrogen to hydrocarbon molar ratio of 2 and a WHSV of 2.7 $h^{-1}$. The results after 4.4 days on stream are summarized in Table 1 below.

TABLE 1

| Wt %, H/C Basis | Feed | Product |
|---|---|---|
| $C_5^-$ | | 8.55 |
| Non-Aromatics | 0.17 | 0.16 |
| Benzene | | 12.87 |
| Toluene | 61.27 | 38.01 |
| Ethylbenzene | 0.03 | 0.06 |
| Xylenes | 0.26 | 30.37 |
| $C_9$ | 29.73 | 8.76 |
| $C_{10}$ | 8.25 | 0.87 |
| $C_{11}+$ | 0.30 | 1.09 |
| Total | 100 | 100 |
| $A_9$ Conversion (%) | | 71 |
| $A_{10}$ Conversion (%) | | 89 |
| De-ethylation Rate (%) | | 98 |
| Xylene Yield (%) | | 30 |
| Ethylbenzene in C8 Aromatics (%) | | 0.19 |
| Ethane/Ethylene | | 4000 |
| Xylene/Ethylbenzene ratio | | 506 |

The results in Table 1 show that the catalyst of Example 1 was highly active, particularly for the de-ethylation rate of the ethylbenzene (de-ethylation rate of 98% and xylene/ethylbenzene ratio of 506). The results in Table 1 also show that the catalyst of Example 1 was highly active for $C_9+$ conversion to xylenes.

EXAMPLE 3

Three grams of the resultant catalyst composition from example 1 was used to effect transalkylation of a mixture of toluene/$C_9+$ aromatic hydrocarbon mixture having the composition given in Table 2 at a temperature of about 412° C., a pressure of 2170 kPAa, a hydrogen to hydrocarbon molar ratio of 2 and a WHSV of 2.7 $h^{-1}$. The results after 4.4 days on stream are summarized in Table 2 below.

TABLE 2

| Wt %, H/C Basis | Feed | Product |
|---|---|---|
| $C_5^-$ | | 14.31 |
| Non-Aromatics | 0.14 | 0.02 |
| Benzene | | 6.09 |
| Toluene | 14.77 | 25.20 |
| Ethylbenzene | 0.01 | 0.07 |
| Xylenes | 0.75 | 33.26 |
| $C_9$ | 67.77 | 17.90 |
| $C_{10}$ | 16.29 | 2.86 |
| $C_{11}+$ | 0.28 | 1.24 |
| Total | 100 | 100 |
| $A_9$ Conversion (%) | | 74 |
| $A_{10}$ Conversion (%) | | 89 |
| De-ethylation Rate (%) | | 98 |
| Xylene Yield (%) | | 33 |
| Ethylbenzene in C8 Aromatics (%) | | 0.20 |
| Ethane/Ethylene | | 13411 |
| Xylene/Ethylbenzene ratio | | 475 |

The results in Table 1 show that the catalyst of Example 1 was highly active, particularly for the de-ethylation rate of the ethylbenzene (de-ethylation rate of 98% and xylene/ethylbenzene ratio of 475). The results in Table 2 also show that the catalyst of Example 1 was highly active for $C_9+$ conversion to xylenes.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A catalyst composition comprising:
   (a) an acidity component having an alpha value of at least 500, said acidity component comprising:
      i) a first molecular sieve consisting of ZSM-12; and
      ii) a second molecular sieve consisting of ZSM-5; and
   (b) a hydrogenation component having hydrogenation activity of at least 1000;
   wherein said catalyst composition is characterized as particulate and wherein said hydrogenation component is incorporated into said acidity component by at least one of ion exchange, incipient wetness impregnation, and solid-state reaction, followed by calcining and then steam treatment.

2. The catalyst composition according to claim 1, wherein said hydrogenation component comprises rhenium.

* * * * *